United States Patent
Nanditale Gurumurthy et al.

(10) Patent No.: US 11,229,480 B2
(45) Date of Patent: Jan. 25, 2022

(54) LATCHING MECHANISM FOR IN-LINE ACTIVATED ELECTROSURGICAL DEVICE

(71) Applicant: COVIDIEN LP, Mansfield, MA (US)

(72) Inventors: Aditya Nanditale Gurumurthy, West Haven, CT (US); Michael B. Lyons, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 951 days.

(21) Appl. No.: 15/875,755

(22) Filed: Jan. 19, 2018

(65) Prior Publication Data
US 2018/0214200 A1 Aug. 2, 2018

Related U.S. Application Data

(60) Provisional application No. 62/453,602, filed on Feb. 2, 2017.

(51) Int. Cl.
*A61B 18/14* (2006.01)
*A61B 18/08* (2006.01)
(Continued)

(52) U.S. Cl.
CPC ........ *A61B 18/1445* (2013.01); *A61B 18/085* (2013.01); *A61B 18/1482* (2013.01);
(Continued)

(58) Field of Classification Search
CPC ............ A61B 18/1442; A61B 18/1445; A61B 18/1447; A61B 2018/1442;
(Continued)

(56) References Cited

U.S. PATENT DOCUMENTS

| D249,549 S | 9/1978 | Pike |
| D263,020 S | 2/1982 | Rau, III |

(Continued)

FOREIGN PATENT DOCUMENTS

| CN | 201299462 Y | 9/2009 |
| DE | 2415263 A1 | 10/1975 |

(Continued)

OTHER PUBLICATIONS

Heniford et al. "Initial Research and Clinical Results with an Electrothermal Bipolar Vessel Sealer" Oct. 1999.
(Continued)

*Primary Examiner* — Linda C Dvorak
*Assistant Examiner* — Annabeth E Rodriguez
(74) *Attorney, Agent, or Firm* — Carter, DeLuca & Farrell LLP

(57) ABSTRACT

A surgical device includes a housing, an elongated shaft, an end effector, and an actuation mechanism. The housing pivotally supports a movable handle between unactuated, first actuated, and a second actuated positions. The elongated shaft extends distally from the housing and defines a longitudinal axis. The end effector has a pair of opposed jaw members that are movable between an open configuration in which the jaw members are spaced apart from one another and a closed configuration in which the jaw members are closer together. The actuation mechanism is configured to transition the end effector between the open and closed configurations as the movable handle is pivoted between the unactuated and first actuated positions and to maintain the end effector in the closed configuration when the moveable handle is between the first and second actuated positions.

11 Claims, 8 Drawing Sheets

(51) Int. Cl.
*A61B 18/00* (2006.01)
*A61B 18/12* (2006.01)
*A61B 17/29* (2006.01)

(52) U.S. Cl.
CPC ... *A61B 18/1206* (2013.01); *A61B 2017/2912* (2013.01); *A61B 2017/2923* (2013.01); *A61B 2018/0063* (2013.01); *A61B 2018/00601* (2013.01); *A61B 2018/00607* (2013.01); *A61B 2018/1455* (2013.01)

(58) Field of Classification Search
CPC ...... A61B 2018/145; A61B 2018/1452; A61B 2018/1455; A61B 2018/1457; A61B 2018/146; A61B 2018/1462
See application file for complete search history.

(56) References Cited

U.S. PATENT DOCUMENTS

| | | | |
|---|---|---|---|
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| D661,394 S | 6/2012 | Romero et al. | |
| D670,808 S | 11/2012 | Moua et al. | |
| D680,220 S | 4/2013 | Rachlin | |
| 9,084,608 B2 | 7/2015 | Larson et al. | |
| 9,211,657 B2 | 12/2015 | Ackley et al. | |
| 2010/0030238 A1* | 2/2010 | Viola | A61B 17/04 606/144 |
| 2013/0053831 A1* | 2/2013 | Johnson | A61B 17/2909 606/1 |
| 2014/0000411 A1* | 1/2014 | Shelton, IV | A61B 34/37 74/650 |
| 2014/0221995 A1 | 8/2014 | Guerra et al. | |
| 2014/0221999 A1 | 8/2014 | Cunningham et al. | |
| 2014/0228842 A1 | 8/2014 | Dycus et al. | |
| 2014/0230243 A1 | 8/2014 | Roy et al. | |
| 2014/0236149 A1 | 8/2014 | Kharin et al. | |
| 2014/0243811 A1 | 8/2014 | Reschke et al. | |
| 2014/0243824 A1 | 8/2014 | Gilbert | |
| 2014/0249528 A1* | 9/2014 | Hixson | A61B 18/1445 606/51 |
| 2014/0250686 A1 | 9/2014 | Hempstead et al. | |
| 2014/0257274 A1 | 9/2014 | Mccullough, Jr. et al. | |
| 2014/0257283 A1 | 9/2014 | Johnson et al. | |
| 2014/0257284 A1 | 9/2014 | Artale | |
| 2014/0257285 A1 | 9/2014 | Moua | |
| 2014/0276803 A1 | 9/2014 | Hart | |
| 2014/0284313 A1 | 9/2014 | Allen, IV et al. | |
| 2014/0288549 A1 | 9/2014 | Mckenna et al. | |
| 2014/0288553 A1 | 9/2014 | Johnson et al. | |
| 2014/0330308 A1 | 11/2014 | Hart et al. | |
| 2014/0336635 A1 | 11/2014 | Hart et al. | |
| 2014/0353188 A1 | 12/2014 | Reschke et al. | |
| 2015/0018816 A1 | 1/2015 | Latimer | |
| 2015/0025528 A1 | 1/2015 | Arts | |
| 2015/0032106 A1 | 1/2015 | Rachlin | |
| 2015/0051598 A1 | 2/2015 | Orszulak et al. | |
| 2015/0051640 A1 | 2/2015 | Twomey et al. | |
| 2015/0066026 A1 | 3/2015 | Hart et al. | |
| 2015/0080880 A1 | 3/2015 | Sartor et al. | |
| 2015/0080889 A1 | 3/2015 | Cunningham et al. | |
| 2015/0082928 A1 | 3/2015 | Kappus et al. | |
| 2015/0088122 A1 | 3/2015 | Jensen | |
| 2015/0088126 A1 | 3/2015 | Duffin et al. | |
| 2015/0088128 A1 | 3/2015 | Couture | |
| 2015/0094714 A1 | 4/2015 | Lee et al. | |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A2 | 3/2003 |

(56) References Cited

FOREIGN PATENT DOCUMENTS

| | | |
|---|---|---|
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/45589 | 6/2002 |
| WO | 06/021269 A1 | 3/2006 |
| WO | 2005110264 A2 | 4/2006 |
| WO | 08/040483 A1 | 4/2008 |
| WO | 2011/018154 A1 | 2/2011 |

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

(56) References Cited

OTHER PUBLICATIONS

Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler, Abandoned.
U.S. Appl. No. 09/177,950, filed Oct. 23, 1998; inventor: Randel A. Frazier, abandoned.
U.S. Appl. No. 09/387,883, filed Sep. 1, 1999; inventor: Dale F. Schmaltz, abandoned.
U.S. Appl. No. 09/591,328, filed Jun. 9, 2000; inventor: Thomas P. Ryan, abandoned.
U.S. Appl. No. 12/336,970, filed Dec. 17, 2008; inventor: Paul R. Sremcich, abandoned.
U.S. Appl. No. 14/065,644, filed Oct. 29, 2013; inventor: Reschke, abandoned.

* cited by examiner

LATCHING MECHANISM FOR IN-LINE ACTIVATED ELECTROSURGICAL DEVICE

CROSS REFERENCE TO RELATED APPLICATION

The present application claims the benefit of and priority to U.S. Provisional Application Ser. No. 62/453,602, filed on Feb. 2, 2017 the entire contents of which are incorporated herein by reference.

BACKGROUND

1. Technical Field

The present disclosure relates to electrosurgical devices and, more specifically, to electrosurgical devices including latching mechanisms to reduce actuation force to maintain the electrosurgical device in a clamped configuration before activation of the device.

2. Discussion of Related Art

Instruments such as electrosurgical forceps are commonly used in open and endoscopic surgical procedures to coagulate, cauterize, and seal tissue. Such forceps typically include a pair of jaws that can be controlled by a surgeon to grasp targeted tissue, such as, e.g., a blood vessel. The jaws may be approximated to apply a mechanical clamping force to the tissue, and are associated with at least one electrode to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis, which may facilitate the transection of the sealed tissue. A detailed discussion of the use of an electrosurgical forceps may be found in U.S. Pat. No. 7,255,697 to Dycus et al.

A bipolar electrosurgical forceps typically includes opposed electrodes disposed on clamping faces of the jaws. The electrodes are charged to opposite electrical potentials such that an electrosurgical current may be selectively transferred through tissue grasped between the electrodes. To affect a proper seal, particularly in relatively large vessels, two predominant mechanical parameters must be accurately controlled; the pressure applied to the vessel and the gap distance established between the electrodes.

Both the pressure and gap distance influence the effectiveness of the resultant tissue seal. If an adequate gap distance is not maintained, there is a possibility that the opposed electrodes will contact one another, which may cause a short circuit and prevent energy from being transferred through the tissue. Also, if too low a force is applied the tissue may have a tendency to move before an adequate seal can be generated. The thickness of a typical effective tissue seal is optimally between about 0.001 and about 0.006 inches. Below this range, the seal may shred or tear and above this range the vessel walls may not be effectively joined. Closure pressures for sealing large tissue structures preferably fall within the range of about 3 $kg/cm^2$ to about 16 $kg/cm^2$.

With some electrosurgical devices, a surgeon first grasps tissue between jaws by partially closes drawing a clamping handle towards a fixed handle until the tissue is grasped between the jaws. When the tissue is grasped and before applying electrosurgical energy to the grasped tissue, the surgeon verifies the position of the jaws and the pressure applied to the tissue before activating electrosurgical energy. When the position is verified, the surgeon applies additional force to the clamping handle to fully close or actuate the clamping handle under the appropriate pressure and activates the electrosurgical device.

While maintaining the clamping handle in a partially closed position to verify the position, surgeons can experience fatigue. It would be advantageous to reduce the force required to maintain the clamping handle in a partially closed position during verification of the position of the jaws. In addition, it would be advantageous to reduce the additional force required to fully close the clamping handle prior to activating the electrosurgical device.

SUMMARY

In an aspect of the present disclosure, a surgical device includes a housing, an elongated shaft, an end effector, and an actuation mechanism. The housing includes a stationary handle and a movable handle pivotally supported by the housing and pivotable between an unactuated position, a first actuated position, and a second actuated position. The elongated shaft extends distally from the housing and defines a longitudinal axis. The end effector is supported by a distal portion of the elongated shaft and has a pair of opposed jaw members that are movable between an open configuration in which the jaw members are spaced apart from one another and a closed configuration in which the jaw members are closer together. The actuation mechanism is configured to transition the end effector between the open configuration and the closed configuration as the movable handle is pivoted between the unactuated position and the first actuated position and to maintain the end effector in the closed configuration when the moveable handle is between the first and second actuated positions.

In aspects, the actuation mechanism includes a segmented gear that is secured to the moveable handle and a first actuation link that is rotatably disposed within the housing. The first actuation link may have a first portion that includes an actuation gear. The segmented gear may be engaged with the actuation gear when the moveable handle is between the unactuated position and the first actuated position and may be disengaged from the actuation gear when the moveable handle is between the first and second actuated positions.

In some aspects, the actuation mechanism includes first, second, and third actuation links. The first actuation link may include first and second portions, and may be rotatable about the first portion such that the second portion is movable in an arc in response to rotation of the first actuation link about the first portion. The second actuation link may include a first portion that is pivotally coupled to the second portion of the first actuation link and a second portion that includes a cam disposed within a cam slot that is defined in a track that is attached to the housing. The third actuation link may include a first portion that is pivotally coupled to the second portion of the section actuation link and a second portion that is coupled to a collar that is translatable along the longitudinal axis of the elongated shaft to transition the end effector between the open and closed configurations. In the unactuated position of the movable handle, the cam may be positioned on a first side of the longitudinal axis and in the first actuated position of the moveable handle the cam may be positioned on a second side of the longitudinal axis. The housing may include a biasing member that is engaged with the collar to urge the collar distally. The biasing member may maintain the cam on the second side of the longitudinal axis when the movable handle is between the first and second actuated positions. The biasing member may be a coil spring that is disposed about the longitudinal axis.

In certain aspects, the actuation gear is disposed on the second side of the longitudinal axis of the elongated shaft. The cam slot may include a first segment that is disposed on the first side of the longitudinal axis and a second segment disposed on the second side of the longitudinal axis. The second segment may be positioned distal of the first segment. The cam slot may be linear or nonlinear.

In particular aspects, the collar may be fixed to an outer shaft that is pivotally coupled to the end effector.

In aspects, the surgical device includes a knife blade and a knife trigger. The knife trigger may be movable when the movable handle is in the second actuated position to advance the knife blade through the end effector. The knife trigger may be prevented from moving when the movable handle is between the unactuated and first actuated positions.

In another aspect of the present disclosure a surgical device includes a moveable handle and an actuation mechanism having a segmented gear, a first link, a second link, a track, a third link, and a collar. The moveable handle includes a boss and is pivotable about the boss between an unactuated position, a first actuated position, and a second actuated position. The actuation mechanism is configured to translate a shaft along a longitudinal axis that is defined by the shaft. The segmented gear is rotatably coupled to the moveable handle about the boss. The first link has a first portion that is selectively engaged by the segmented gear and defines an opening and a second portion that rotates about the opening in response to engagement between the first portion and the segmented gear. The second link has a first segment and a cam. The first segment is rotatably coupled to the second portion of the first link. The track defines a cam slot that slidably receives the cam. The cam slides within the cam slot in response to rotation of the second portion of the first link. The third link has a first portion that is rotatably coupled to the cam and a second portion. The collar is coupled to the second portion of the third link and is configured to translate the shaft in response to sliding of the cam within the cam slot.

In aspects, the cam slot includes first and second parts. The collar may be disposed in a first position along the longitudinal axis of the shaft when the cam is in the first part of the cam slot and the collar may be positioned in a second position along the longitudinal axis proximal of the first position when the cam is in the second part of the cam slot. The second part may be positioned distal of the first part. The cam may be disposed on a first side of a center of the collar when positioned in the first part of the cam slot and on a second side of the center of the collar, opposite the first side, when positioned in the second part of the cam slot.

In some aspects, the surgical device includes a biasing member that is engaged with the collar and is configured to maintain the cam in the second part of the cam slot to urge the cam away from the second part when the cam is positioned in the first part.

In another aspect of the present disclosure, a method of sealing tissue with a surgical device includes positioning targeted tissue between jaw members of an end effector of a surgical device with the jaw members in an open configuration, compressing a moveable handle of the surgical device from an unactuated position to a first actuated position such that the jaw members are transitioned to a clamped configuration, and compressing the movable handle from the first actuated position to a second actuated position beyond the first actuated position to activate delivery of electrosurgical energy to the targeted tissue between the jaw members. The surgical device maintains the jaw members in the clamped configuration when the movable handle is in the first actuated position. The movable handle is mechanically decoupled from the end effector between the first and second actuated positions.

In aspects, compressing the movable handle from the unactuated position to the first actuated position includes engaging a first link with a segmented gear coupled to the movable handle to rotate the first link about an opening defined in a first portion to transition the jaw members to the clamped configuration. Compressing the movable handle from the first actuated position to the second actuated position includes disengaging the segmented gear from the first link such that the movable handle is free to move independent of the jaw members between the first and second actuated positions. Compressing the movable handle from the first actuated position to the second actuated position includes activating a button with the movable handle to activate delivery of electrosurgical energy.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
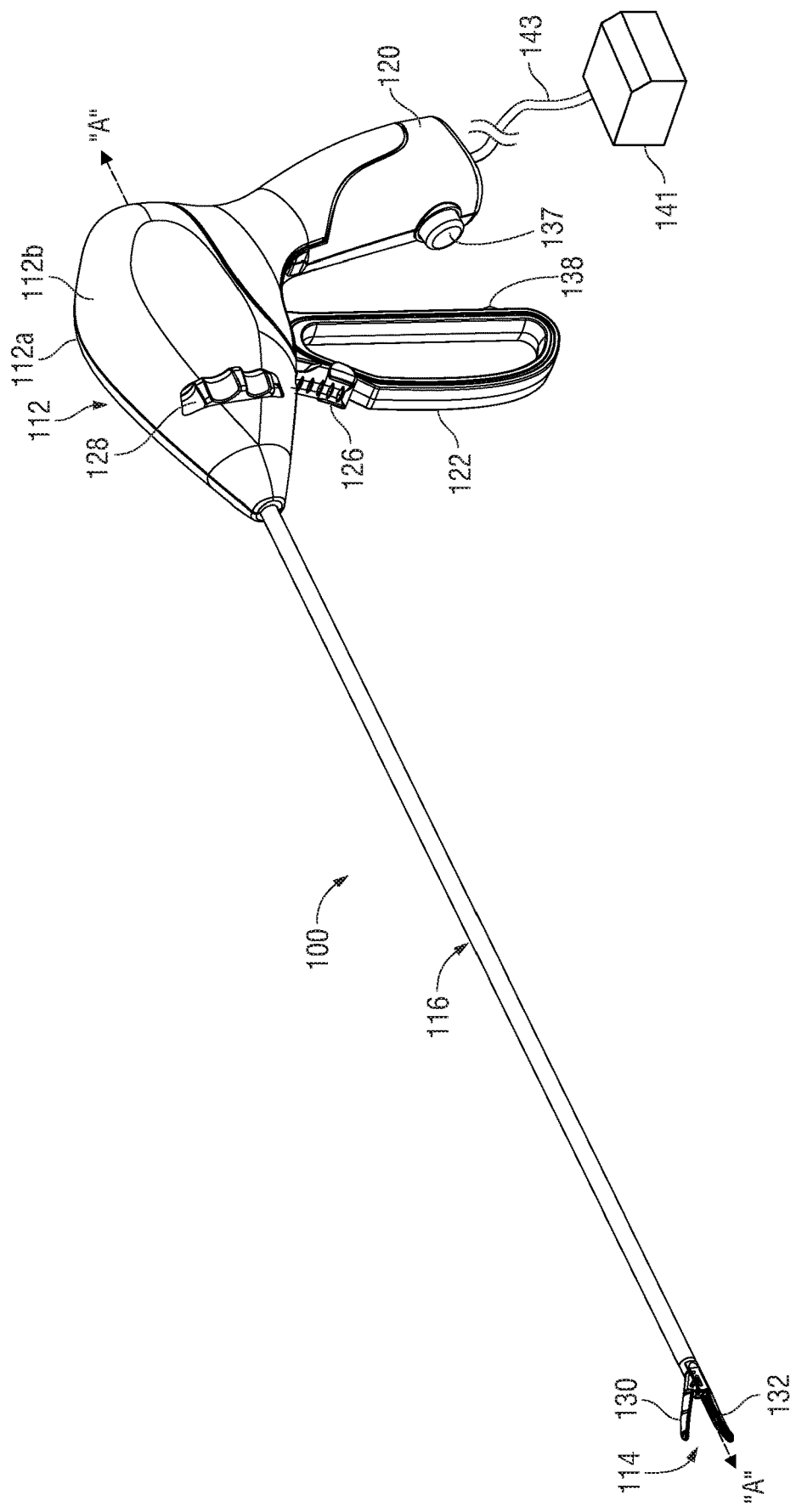
FIG. 1 is a is a perspective view of an electrosurgical forceps according to the present disclosure including a housing, an elongated shaft, and an end effector.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Referring initially to FIG. 1, an embodiment of an electrosurgical forceps 100 generally includes a housing 112 that supports various actuators thereon for remotely controlling an end effector 114 through an elongated shaft 116. Although this configuration is typically associated with instruments for use in laparoscopic or endoscopic surgical procedures, various aspects of the present disclosure may be practiced with traditional open instruments and in connection with certain endoluminal procedures.

The housing 112 is constructed of a left housing half 112a and a right housing half 112b. The left and right designation of the housing halves 112a, 112b refer to the respective directions as perceived by an operator using the forceps 100. The housing halves 112a, 112b are constructed of sturdy plastic, and are joined to one another by adhesives, ultrasonic welding or other suitable assembly methods.

To mechanically control the end effector 114, the housing 112 supports a stationary handle 120, a movable handle 122, a trigger 126 and a rotation knob 128. The movable handle 122 is operable to move the end effector 114 between an open configuration (FIG. 2A) wherein a pair of opposed jaw members 130, 132 are disposed in spaced relation relative to one another, and a closed or clamping configuration (FIG. 2B) wherein the jaw members 130, 132 are closer together. Approximation of the movable handle 122 with the stationary handle 120 serves to move the end effector 114 to the closed configuration and separation of the movable handle 122 from the stationary handle 120 serves to move the end effector 114 to the open configuration. In some embodiments, the movable handle 122 may be shaped to facilitate spring-biased separation of the movable handle 122 from the stationary handle 120 to move the end effector 114 from the closed configuration to the open configuration, as discussed in detail hereinbelow.

The trigger 126 is operable to extend and retract a knife blade 156 (see FIGS. 2A and 2B) through the end effector 114 when the end effector 114 is in the closed configuration. The rotation knob 128 serves to rotate the elongated shaft 116 and the end effector 114 about a longitudinal axis A-A extending through the forceps 100.

Figure 7:
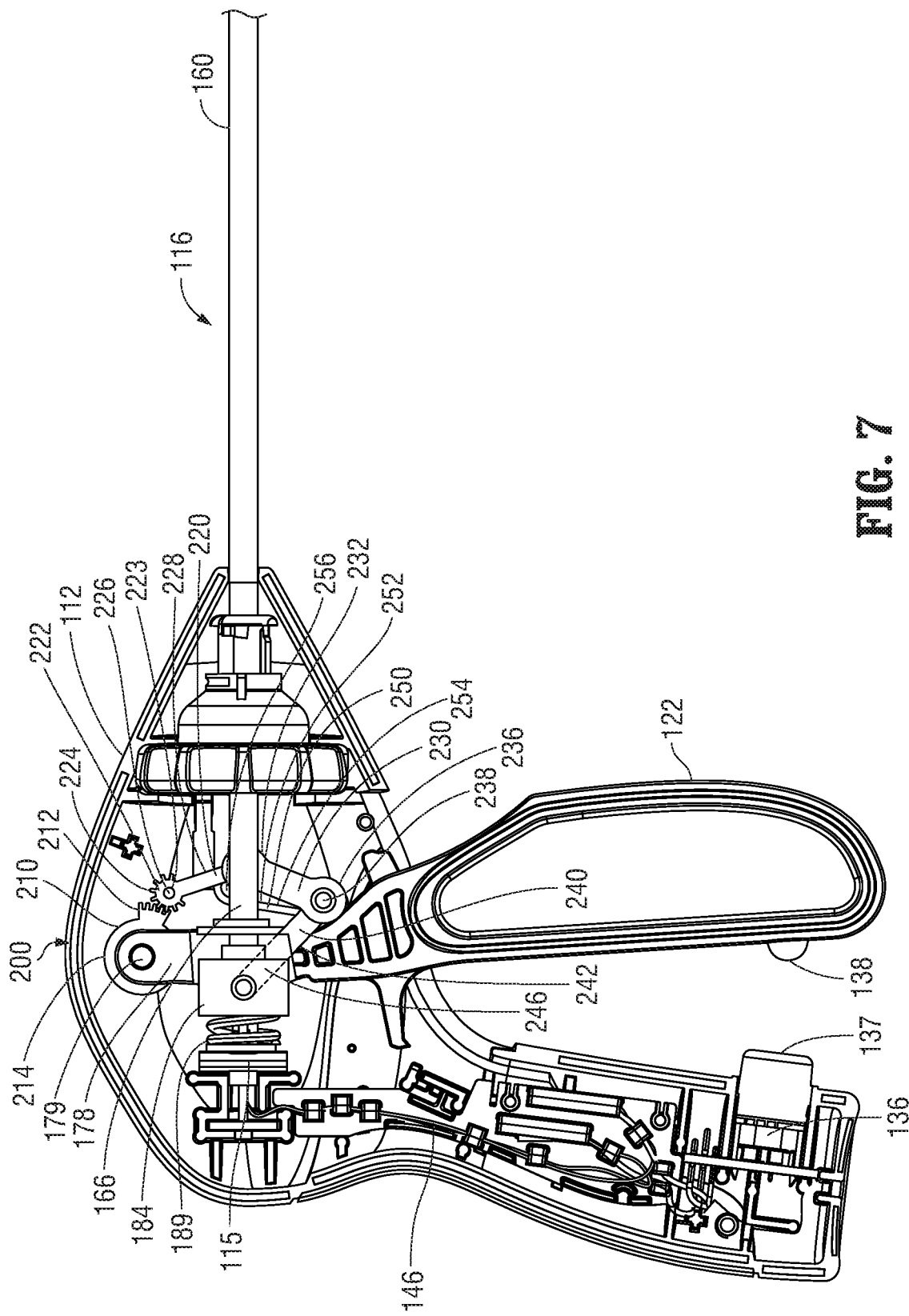
FIG. 7 is an internal, side view of the proximal portion of the instrument of FIG. 6 illustrating a movable handle in an unactuated position with respect to a stationary handle, with an outer tube in a distal position which corresponds to the open configuration of the end effector depicted in FIG. 2A.
Figure 8:
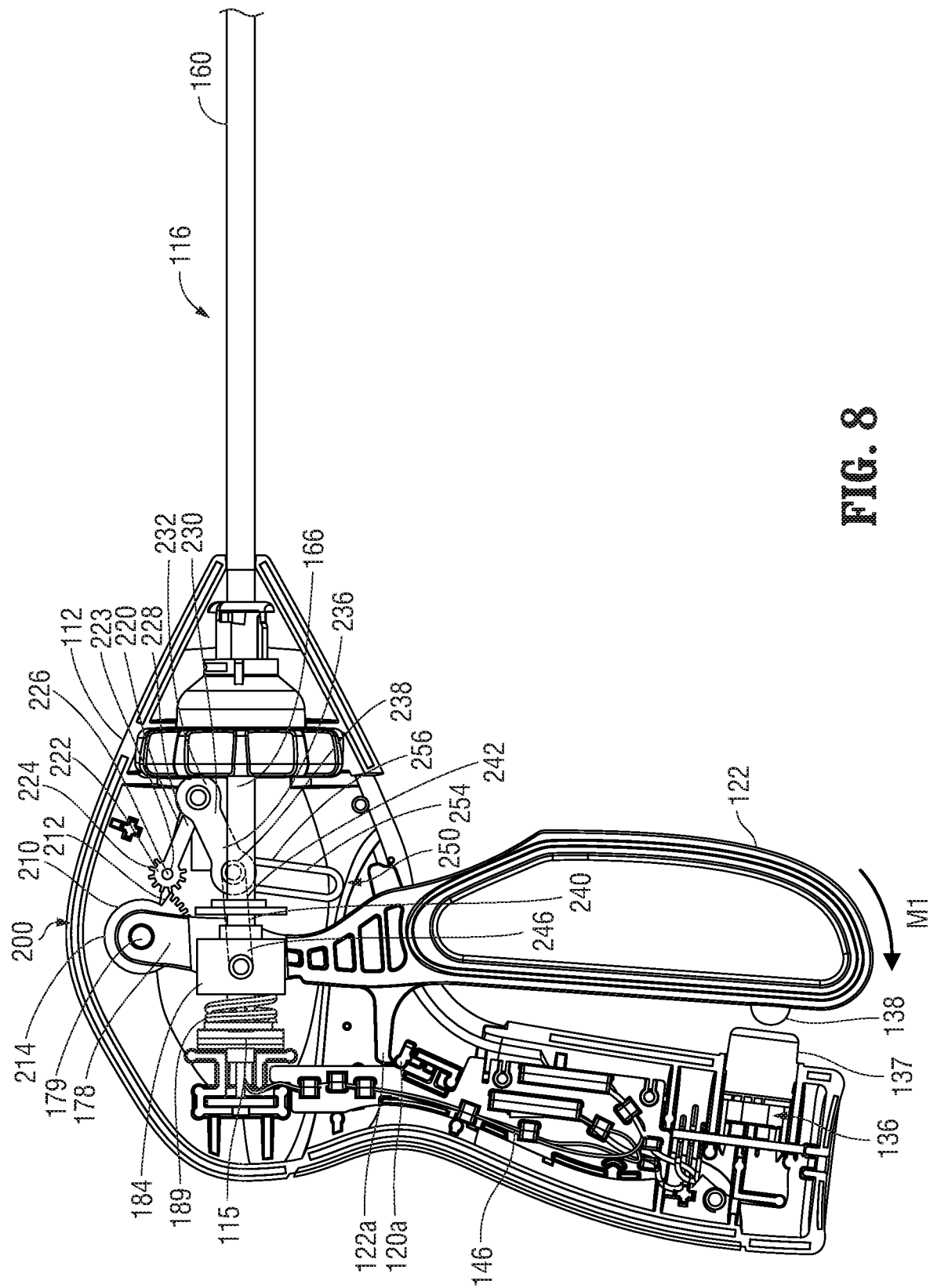
FIG. 8 is an internal, side view of the proximal portion of the instrument of FIG. 6 illustrating the movable handle in a first actuated position with respect to the stationary handle, with the outer tube in a proximal position which corresponds to a clamped configuration of the end effector depicted in FIG. 2B.
Figure 9:
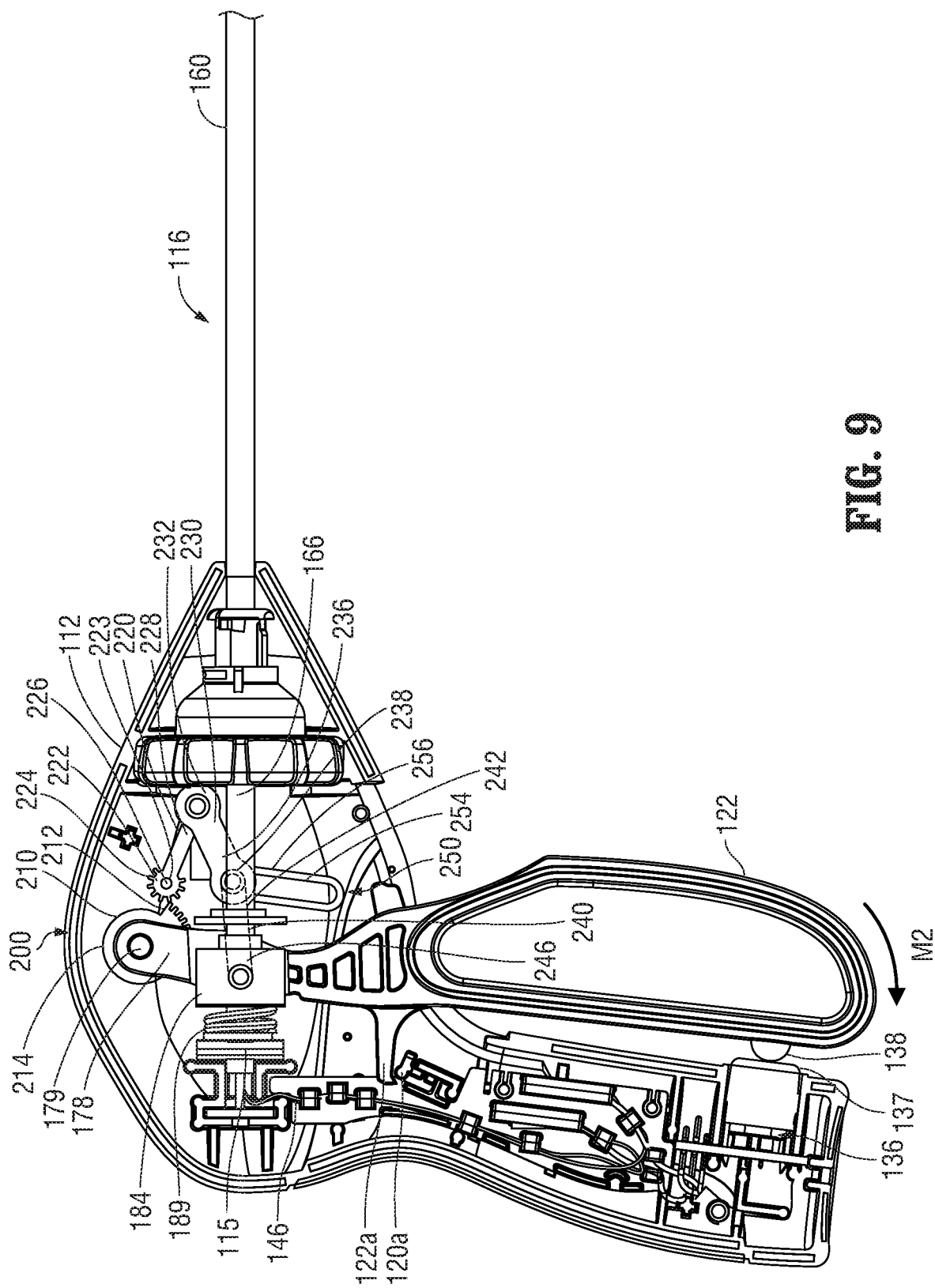
FIG. 9 is an internal, side view of the proximal portion of the instrument of FIG. 6 illustrating the movable handle in a second actuated position with respect to the stationary handle, with the outer tube maintained in the proximal position by an actuation mechanism to maintain the end effector in the closed configuration depicted in FIG. 2B.

To electrically control the end effector 114, the stationary handle 120 supports a depressible button 137 thereon, which is operable by the user to initiate and terminate the delivery of electrosurgical energy to the end effector 114. More specifically, and as illustrated in FIGS. 7-9, the depressible button 137 is mechanically coupled to a switch 136 disposed within the stationary handle 120 and is engagable by a button activation post 138 extending from a proximal side of the movable handle 122 upon proximal movement of the movable handle 122 to a fully actuated or proximal position as depicted in FIG. 9. The switch 136 is in electrical communication with a source of electrosurgical energy such as electrosurgical generator 141 or a battery (not shown) supported within the housing 112. The generator 141 may include devices such as the LIGASURE® Vessel Sealing Generator and the FORCE TRIAD® Generator sold by Covidien. A cable 143 extends between the housing 112 and the generator 141 and includes a connector (not shown) thereon such that the forceps 100 may be selectively coupled and decoupled electrically from the generator 141.

Figure 2A:
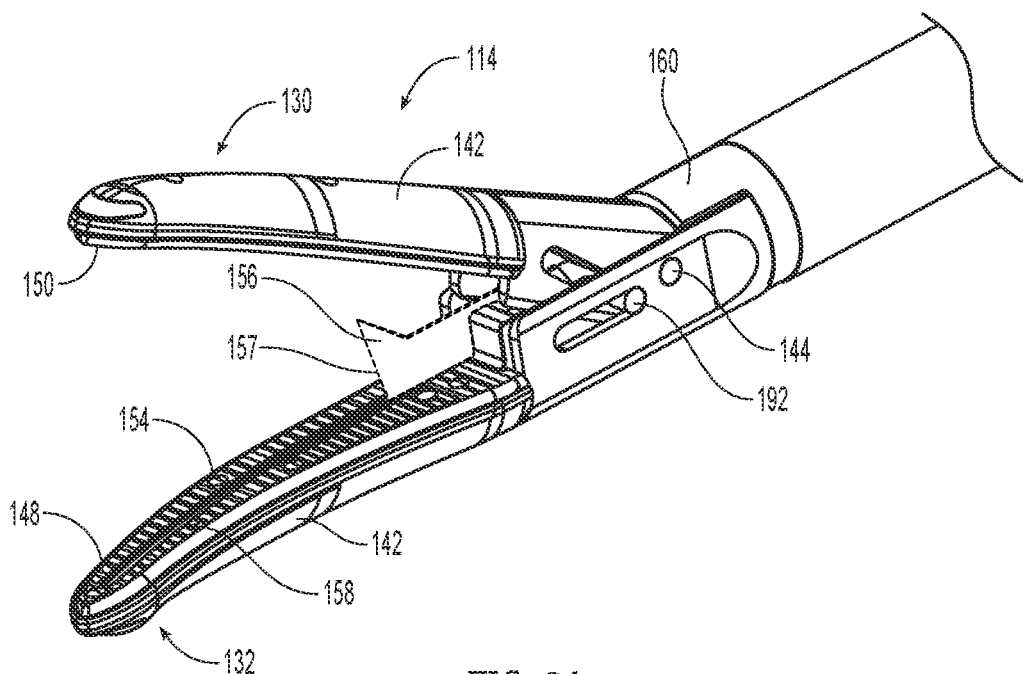
FIG. 2A is an enlarged, perspective view of the end effector of FIG. 1 illustrating a pair of jaw members in an open configuration and a knife.
Figure 2B:
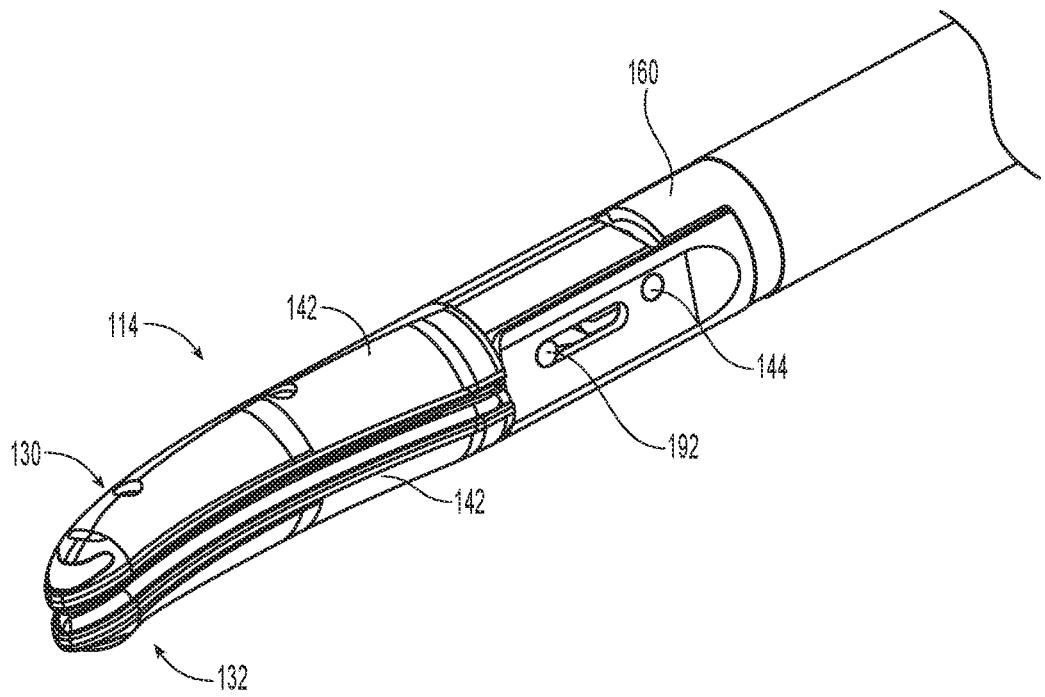
FIG. 2B is an enlarged, perspective view of the end effector of FIG. 1 illustrating the pair of jaw members in a clamped configuration.
Figure 3:
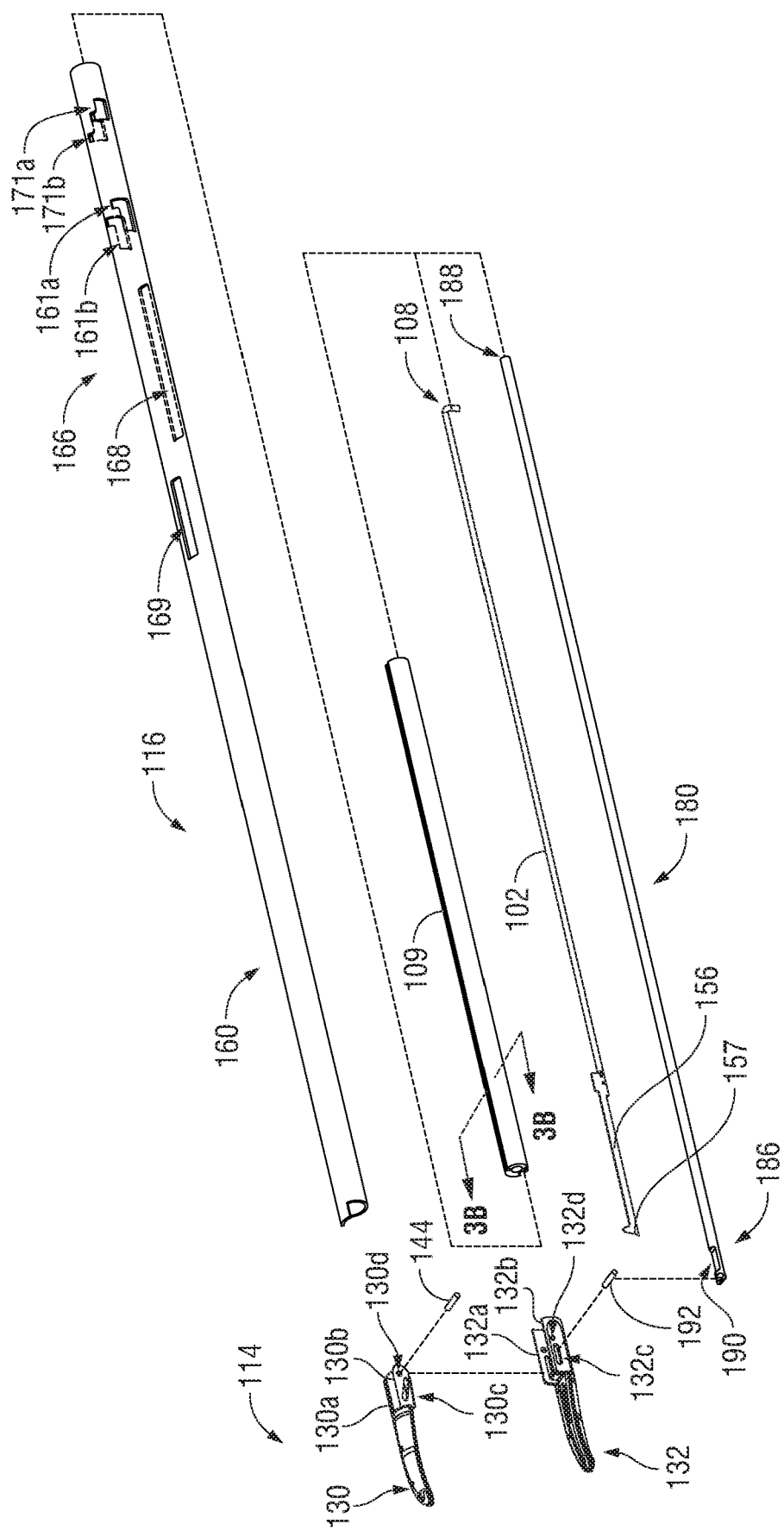
FIG. 3 is a perspective view of the end effector and the elongated shaft of FIG. 1 with parts separated.

Referring now to FIGS. 2A-3, the end effector 114 may be moved from the open configuration (FIG. 2A) wherein tissue (not shown) is received between the jaw members 130, 132, and the closed configuration (FIG. 2B), wherein the tissue is clamped and sealed. The upper and lower jaw members 130, 132 are electrically coupled to cable 143, and thus to the generator 141 (e.g., via respective wires 146 (FIGS. 7-9) extending through the elongated shaft 116) to provide an electrical pathway to a pair of electrically conductive, tissue-engaging sealing plates 148, 150 disposed on the lower and upper jaw members 132, 130, respectively. The sealing plate 148 of the lower jaw member 132 opposes the sealing plate 150 of the upper jaw member 130, and, in some embodiments, the sealing plates 148 and 150 are electrically coupled to opposite terminals, e.g., positive or active (+) and negative or return (−) terminals associated with the generator 141. Thus, bipolar energy may be provided through the sealing plates 148 and 150. Alternatively, the sealing plates 148 and 150 and/or the end effector 114 may be configured for delivering monopolar energy to the tissue. In a monopolar configuration, one or both sealing plates 148 and 150 deliver electrosurgical energy from an active terminal, e.g. (+), while a return pad (not shown) is placed generally on a patient and provides a return path to the opposite terminal, e.g. (−), of the generator 141. Each jaw member 130, 132 includes a jaw insert 140 and an insulator 142 that serves to electrically insulate the sealing plates 150, 148 from the jaw insert 140 of jaw members 130, 132, respectively.

Figure 6:
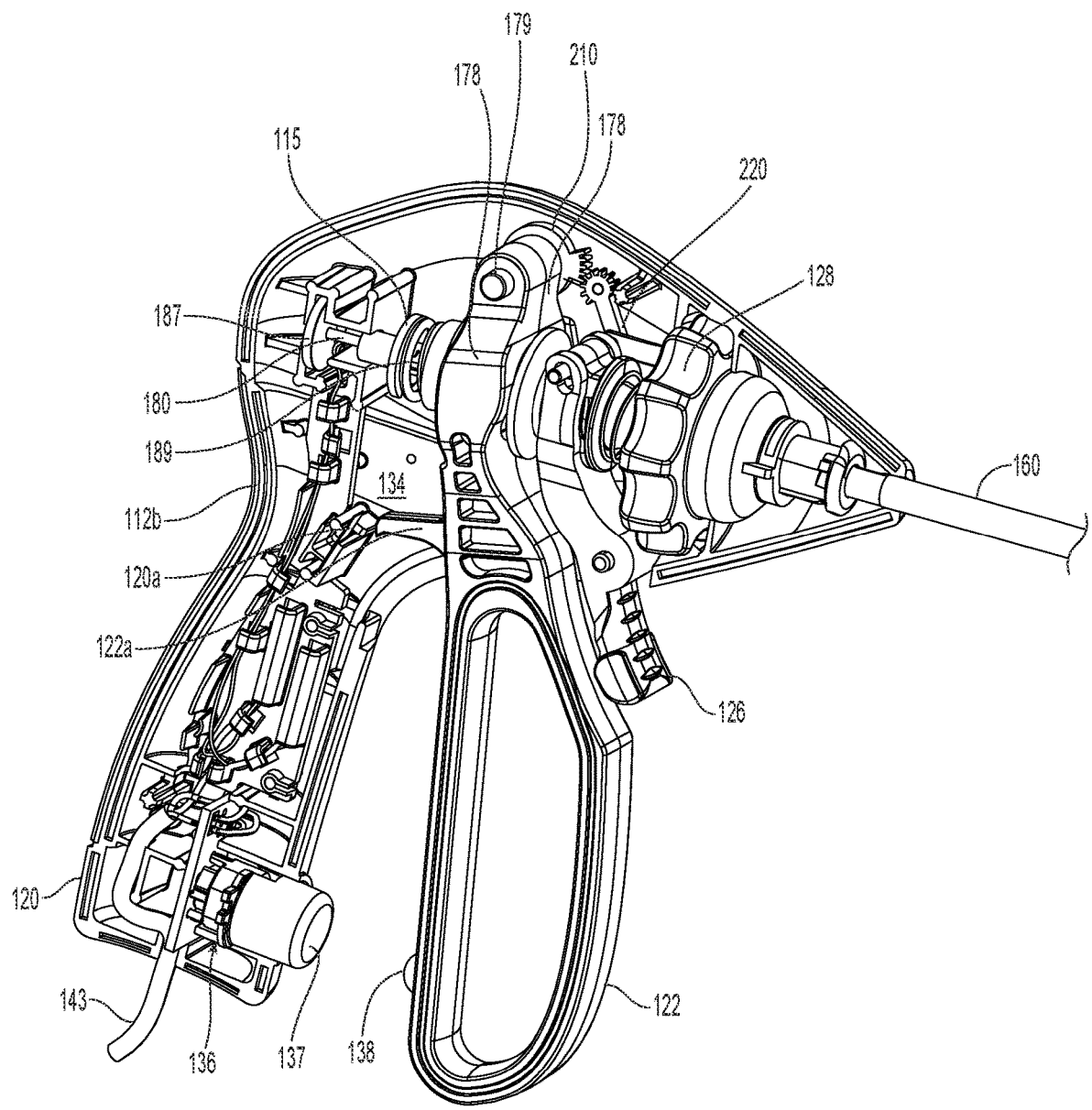
FIG. 6 is a perspective view of a proximal portion of the instrument of FIG. 1 with a portion of the housing removed revealing internal components thereof.

Referring to FIG. 3, the elongated shaft 116 includes various longitudinal components that operatively couple the end effector 114 to the various actuators supported by the housing 112 (FIG. 1). An outer shaft member 160 defines an exterior surface of the elongated shaft 116 and supports movement of other components therethrough. The outer shaft member 160 is configured for longitudinal motion with respect to an inner actuation member 180 axially received within the outer shaft member 160. The inner actuation member 180 may be a rod, shaft, stamped metal, or other suitable mechanical component. A proximal portion 166 of the outer shaft member 160 is configured for receipt within the housing 112 (FIG. 1), and includes features for operatively coupling the outer shaft member 160 to the actuators supported thereon, e.g. the movable handle 122. A distal portion 186 of the inner actuation member 180 includes a longitudinal recess 190 defined therein that provides clearance for the pivot pin 144 and thus, permits longitudinal reciprocation of the pivot pin 144 (via longitudinal reciprocation of the outer shaft member 160) independent of the inner actuation member 180. Distally of the longitudinal recess 190, the cam pin 192 is mechanically coupled (e.g., via welding, friction-fit, laser welding, etc.) to the distal portion 186 of the inner actuation member 180. A proximal portion 188 of the inner actuation member 180 includes a washer 187 coupled thereto (FIG. 6). The washer 187 is supported within the housing 112 and serves to prohibit longitudinal motion of the inner actuation member 180 along the longitudinal axis A-A.

Referring back to FIGS. 2A and 2B, the jaw members 130, 132 may be pivoted about the pivot pin 144 to move the end effector 114 to the closed configuration of FIG. 2B wherein the sealing plates 148, 150 provide a pressure to tissue grasped therebetween. In some embodiments, to provide an effective seal, a pressure within a range between about 3 kg/cm$^2$ to about 16 kg/cm$^2$ and, in embodiments, within a working range of 7 kg/cm$^2$ to 13 kg/cm$^2$ is applied to the tissue. Also, in the closed configuration, a separation or gap distance "G" may be maintained between the sealing plates 148, 150 by an array of stop members 154 (FIG. 2A) disposed on or adjacent the sealing plates 148, 150. The stop members 154 contact opposing surfaces on the opposing jaw member 130, 132 and prohibit further approximation of the sealing plates 148, 150. In some embodiments, to provide an effective tissue seal, an appropriate gap distance of about 0.001 inches to about 0.010 inches and, in embodiments, between about 0.003 inches and about 0.006 inches may be provided. In some embodiments, the stop members 154 are constructed of an electrically non-conductive plastic or other material molded onto the jaw members 130, 132, e.g., by a process such as overmolding or injection molding. In other embodiments, the stop members 154 are constructed of a heat-resistant ceramic deposited onto the jaw members 130, 132.

Electrosurgical energy may be delivered to the tissue through the electrically conductive seal plates 148, 150 to affect a tissue seal. Once a tissue seal is established, a knife blade 156 having a sharp distal cutting edge 157 may be advanced through a knife channel 158 defined in one or both jaw members 130, 132 to transect the sealed tissue. Knife blade 156 is depicted in FIG. 2A as extending from the elongated shaft 116 when the end effector 114 is in an open configuration. In some embodiments, a knife lockout is provided to prevent extension of the knife blade 156 into the knife channel 158 when the end effector 114 is in the open configuration.

The proximal portion 166 of the outer shaft member 160 includes various features that serve to couple the outer shaft member 160 to various elements of the housing 112. More specifically, the proximal portion 166 of the outer shaft member 160 includes, in order from distal to proximal, a longitudinal slot 169 extending distally from a proximal portion thereof to couple the outer shaft member 160 to the rotation knob 128, a longitudinal knife slot 168 defined therethrough, a pair of opposing distal locking slots 161a, 161b, and a pair of opposing proximal locking slots 171a, 171b. The connection established between the outer shaft member 160 and the rotation knob 128 is described below with reference to FIG. 4.

The pivot pin 144 extends through a proximal portion of each of the jaw members 130, 132 to pivotally support the jaw members 130, 132 at the distal portion of the outer shaft member 160. With reference to FIG. 8, a proximal portion of each of the jaw members 130, 132 includes two laterally spaced parallel flanges or "flags" 130a, 130b and 132a, 132b, respectively, extending proximally from a distal portion of the jaw members 130 and 132. A lateral cam slot 130c and a lateral pivot bore 130d extend through each of the flags 130a, 130b of the upper jaw member 130. Similarly, a lateral cam slot 132c and a lateral pivot bore 132d extend through each of the flags 132a, 132b of the lower jaw member 132. The pivot bores 130d, 132d receive the pivot pin 144 in a slip-fit relation that permits the jaw members 130, 132 to pivot about the pivot pin 144 to move the end effector 114 between the open and closed configurations (FIGS. 2A and 2B, respectively).

A knife rod 102 is coupled (e.g., via welding) at a distal-most end to the sharpened knife blade 156 and includes an angled proximal end 108 that provides a mechanism for operatively coupling the knife rod 102 to the trigger 126. For a detailed description of the connection between the knife rod 102 and the trigger 126 reference can be made to U.S. Patent Publication No. 2014/0257284, the entire contents of which are hereby incorporated by reference. The sharp cutting edge 157 of the knife blade 156 may be applied to the distal end of the knife blade 156 subsequent to the stamping process that forms the profile. For example, various manufacturing techniques may be employed such as grinding, coining, electrochemical etching, electropolishing, or other suitable manufacturing processes, for forming sharpened edges.

A tube guide 109 is disposed within the outer shaft member 160 and includes a central guide lumen 107 axially disposed therethrough and a longitudinal guide recess 105 formed therein. The inner actuation member 180 is received within the central guide lumen 107, which serves to guide longitudinal motion of the inner actuation member 180 within the outer shaft member 160. The knife rod 102 is received within the longitudinal recess 105, which serves to guide longitudinal motion of the knife rod 102 within the outer shaft member 160. In this way, the inner actuation member 180 and the knife rod 102 are aligned within the outer shaft member 160 by the tube guide 109 such that the inner actuation member 180 and the knife rod 102 are free to move longitudinally relative to and in parallel with each other.

Figure 4:
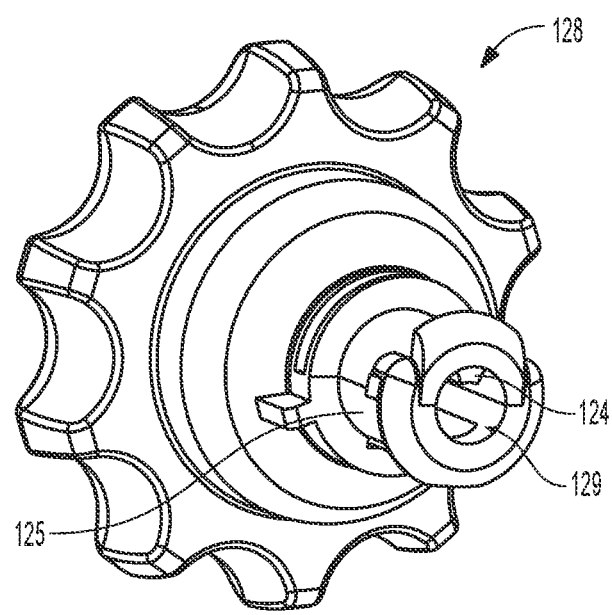
FIG. 4 is a proximally-facing, perspective view of a rotation knob depicting a passageway for receiving the elongated shaft of FIG. 1.

Referring now to FIG. 4, the rotation knob 128 includes a passageway 129 defined therethrough for receiving the outer shaft member 160. The passageway 129 has a generally circular profile corresponding to the circular profile of the outer shaft member 160. The passageway 129 and the outer shaft member 160 may have other corresponding profiles including, but not limited to, triangular, rectangular, pentagonal, hexagonal, or octagonal. The passageway 129 includes a longitudinal keying member 124 that is configured to align with and be seated within longitudinal slot 169 (FIG. 3A) of the outer shaft member 160. The keying member 124 projects laterally inward along the length of passageway 129 such that the insertion of the proximal portion of the outer shaft member 160 into the passageway 129 of the rotation knob 128 operatively couples the outer shaft member 160 to the rotation knob 128 and, thus, permits longitudinal motion of the inner actuation member 180 therethrough. Rotational motion imparted to the rotation knob 128 may thus impart rotational motion to each of the components of the elongated shaft 116, and to the end effector 114, coupled thereto. As shown in FIG. 6, the rotation knob 128 is seated within an interior compartment 134 defined in the housing 112 and, as shown in FIG. 1, extends laterally outward from opposing sides of the housing 112 (only shown extending laterally outward from housing half 112b).

Figure 5:
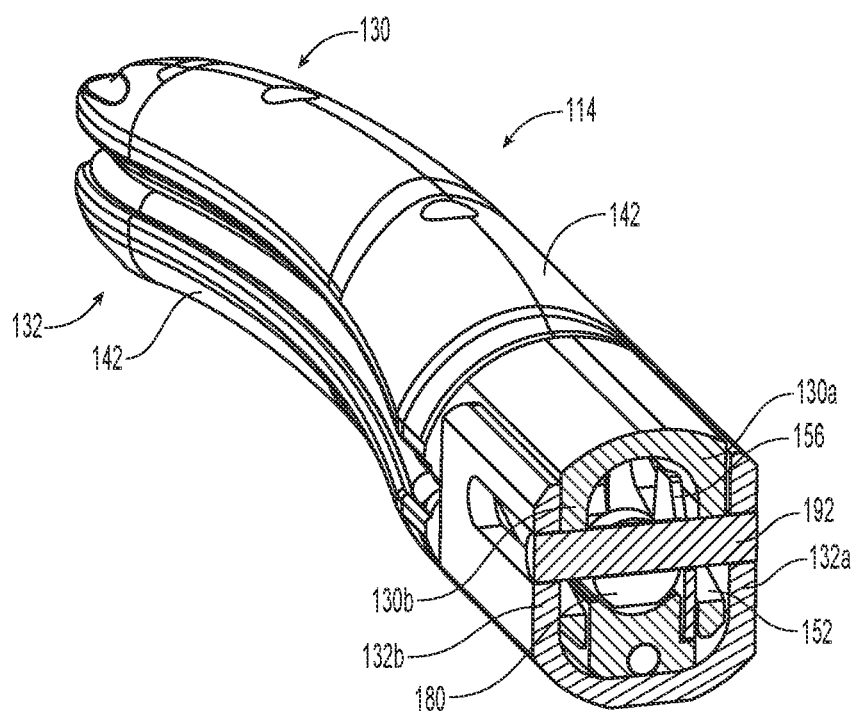
FIG. 5 is an enlarged, cross-sectional, perspective view of the end effector of FIG. 1.

Referring now to FIG. 5, the end effector 114 is coupled to the distal portion of the inner actuation member 180 by the cam pin 192. The inner actuation member 180, and thus the cam pin 192, remains stationary as the outer shaft member 160, the pivot pin 144, and the knife rod 102 move longitudinally. The cam pin 192 extends through flags 132a, 132b of the lower jaw member 132 and flags 130a and 130b of the upper jaw member 130. For additional detail of end effector 114, reference can be made to U.S. Patent Publication Nos. 2014/0257274 and 2014/0257284 and U.S. Pat.

No. 9,456,863. The entire contents of each of these disclosures are incorporated by reference herein.

Referring now to FIGS. 6-9, the connection of the movable handle 122 and the elongated shaft 116 for translation of the outer shaft member 160 is described. As discussed above, translation of the outer shaft member 160 serves to move the end effector 114 between the open configuration of FIG. 2A and the closed configuration of FIG. 2B.

The movable handle 122 is operably coupled to the outer shaft member 160 by an actuation mechanism 200 that is configured to translate the outer shaft member 160 between an open position (FIG. 7) corresponding to the open configuration (FIG. 2A) of the end effector 114 and a closed position (FIG. 8) corresponding to the closed configuration (FIG. 2B) of the end effector 114. The movable handle 122 has an unactuated or distal position (FIG. 7), a first or partially actuated position (FIG. 8), and a second or fully actuated position (FIG. 9). As detailed below, when the movable handle 122 is in the unactuated position, the end effector 114 is in the open configuration and when the movable handle 122 is in the first actuated position, the end effector 144 is in the closed configuration, and when the movable handle 122 is in the fully actuated position, the end effector 144 is maintained in the closed configuration and the depressible button 137 is engaged by the button activation post 138 of the movable handle 122.

With particular reference to FIG. 7, the movable handle 122 includes a clevis 178 disposed about the outer shaft 160. The clevis 178 is pivotally coupled within the housing 112 by bosses 179 extending from a top portion of the clevis 178 that are positioned above the outer shaft 160.

The actuation mechanism 200 includes a segmented gear 210, a first actuation link 220, a second actuation link 230, and a third actuation link 240. The segmented gear 210 is coaxially disposed with the bosses 179 and is pivotally fixed to the clevis 178 such that as the movable handle 122 is pivoted about the bosses 179, the segmented gear 210 rotates about the bosses 179. The segmented gear 210 may be unitarily or monolithically formed with the clevis 178. The segmented gear 210 includes a geared segment 212 and a non-geared segment 214. As shown, the geared segment 212 may be disposed along about 20° of the outer surface of the segmented gear 210 which corresponds to the angular distance that the movable handle 122 rotates about the bosses 179 between the unactuated position and the first actuated position. The geared segment 212 may be disposed along a range of about 10° to about 45° of the outer surface of the segmented gear 210.

The first actuation link 220 includes a first portion 222 and a second portion 228. The first portion 222 includes an actuation gear 224 and is pivotally coupled within the housing 112. The first portion 222 may define an opening 226 that receives a pin 223 secured in the housing 112. The first portion 222 is positioned such that the actuation gear 224 meshes with the geared segment 212 of the segmented gear 210 as the movable handle 122 is pivoted between the unactuated position and the first actuated position and is disengaged from the geared segment 212 when the movable handle 122 is pivoted between the first actuated position and the second actuated position. The second portion 228 of the first actuation link 220 rotates about the first portion 222 in response to engagement between the geared segment 212 and the actuation gear 224.

The second actuation link 230 includes a first portion 232 and a second portion 236. The first portion 232 is pivotally coupled to the second portion 228 of the first actuation link 220 and moves in an arc centered about the pin 223 in response to rotation of the first actuation link 220. The second portion 236 of the second actuation link 230 includes a cam 238. The cam 238 is disposed within a track 250 secured to the housing 112. As shown, the track 250 defines a linear cam slot 252 with a first portion 254 positioned below a centerline of the outer shaft 160 and a second portion 256 positioned above the centerline of the outer shaft 160. The linear cam slot 252 is disposed substantially vertically with the second portion 256 positioned distal to the first portion 254. The track 250 may be non-linear. In such embodiments, the track 250 may include a locking notch (not shown) that receives the cam 238 when the end effector 114 is in the clamped configuration. When the cam 238 is disposed in the first portion 254 of the track 250, the cam 238 is positioned below the centerline of the outer shaft 160 and when the cam 238 is positioned at a second end 258 of the second portion 256 of the track 250, the cam 238 is positioned above the centerline of the shaft 160.

The third actuation link 240 includes a first portion 242 pivotally coupled to the second portion 236 of the second actuation link 230 and a second portion 246 pivotally coupled to a collar 184 disposed about a second portion 166 of the outer shaft 160. The collar 184 is fixed to the second portion 166 such that the outer shaft 160 longitudinally translates in response to translation of the collar 184. The outer shaft 160 limits translation of the collar 184 to translation along the longitudinal axis of the outer shaft 160. A biasing member 189 is disposed about the outer shaft 160 and is positioned between a collar 184 and a stop 115 that biases the collar 184, and thus the outer shaft 160, distally.

With continued reference to FIGS. 7-9, the actuation mechanism 200 operably couples the movable handle 122 to the end effector 114 (FIG. 1) to move the end effector 114 between the open configuration (FIG. 2A) and the clamped configuration (FIG. 2B) and operably decouples the movable handle 122 from the end effector 114 to allow the movable handle 122 to move freely between a first actuated position and a second actuated position while maintaining the end effector 114 in the clamped configuration.

Initially referring to FIG. 7, with the movable handle 122 in the unactuated position, the cam 138 is positioned in the first portion 254 of the track 250 and the collar 184, and thus the outer shaft, is in a distal or open position such that the end effector 114 is in the open configuration (FIG. 2A). In the unactuated position of the movable handle 122, the geared segment 212 of the segmented gear 210 meshes with the actuation gear 224 of the first actuation link 220. The biasing member 189 engages the collar 184 to urge the collar 184 to bias the movable handle 122 to the unactuated position through interaction with the actuation mechanism 200.

With reference to FIG. 8, as the movable handle 122 is compressed or actuated towards the stationary handle 120, as indicated by arrow M1, pivoting of the movable handle 122 affects rotation of the segmented gear 210 about the bosses 179. The segmented gear 210 meshes with the actuation gear 224 such that rotation of the segmented gear 210 affects rotation of the first actuation link 220 about the pin 223 as the movable handle 122 is actuated to the first actuated position as shown in FIG. 8. The first portion 232 moves in an arc in response to rotation of the first actuation link 220 to slide the cam 238 into the second portion 256 of the cam slot 252. As the cam 238 slides towards the second portion 256 of the cam slot 252, the third actuation link 240 moves the collar 184 proximally against the bias member 189. As the collar 184 moves proximally in response to the actuation link 240, the outer shaft 160 is moved to a proximal or clamped position such that the end effector 114 transitions to the closed configuration as shown in FIG. 2B.

When the collar 184 reaches the proximal position as shown in FIG. 8, the cam 238 is positioned above the centerline of the outer shaft 160 and the segmented gear 212 disengages the actuation gear 224. When the cam 238 is positioned above the centerline of the outer shaft 160, the biasing member 189 urges the collar 184 distally such that the cam 238 is urged towards the second portion 256 of the cam slot 252 to maintain the end effector 114 in the closed configuration. It will be appreciated that the biasing member 189 may be calibrated such that the end effector 114 maintains a closure pressure within the range of about 3 kg/cm$^2$ to about 16 kg/cm$^2$. With the biasing member 189 urging the cam 238 into the second portion 256, the movable handle 122 can be released with the basing member 189 maintaining the end effector 114 in the closed configuration.

Referring now to FIG. 9, during actuation of the movable handle 122 between the first actuated position and the second actuated position the segmented gear 212 disengages or decouples from the actuation gear 224. Decoupling the segmented gear 212 and the actuation gear 224 allows the movable handle 122 to move between the first and second actuated positions without affecting the position of the collar 184 and thus, the configuration of the end effector 114. In addition, decoupling the segmented gear 212 and the actuation gear 224 allows the movable handle 122 to move between the first and second actuated positions with reduced force. This reduced force provides feedback to the clinician that further actuation in direction M2 of the movable handle 122 will cause the button activation post 138 to engage the depressible button 137.

Additionally or alternately, as the movable handle 122 approaches the second actuated position, a tooth 122a extending proximally from an upper portion of the movable handle 122 engages a clicker tab 120a supported within the stationary handle 120 to generate a tactile and/or audio response. This response generated by the clicker tab 120a corresponds to a complete grasping of tissue between the jaw members 130, 132 (FIGS. 2A, 2B) and serves to indicate to the surgeon that further proximal actuation of the movable handle 122 will cause the button activation post 138 to engage the depressible button 137.

As the movable handle 122 is moved from the from the first actuated position (FIG. 8) to the second actuated position (FIG. 9), the button activation post 138 depresses the depressible button 137, thereby activating the switch 136 disposed within the stationary handle 120 to initiate the delivery of electrosurgical energy to the end effector 114 to generate a tissue seal.

When the movable handle is in the second actuated position, the knife trigger 126 (FIG. 1) may be selectively moved from a distal position to a proximal position to advance the knife blade 156 distally through knife channel 158 (FIG. 2B). For additional details of the coupling of the knife trigger 126 to the knife blade 156, reference can be made to the previously mentioned U.S. Patent Publication Nos. 2014/0257274 and 2014/0257284 and U.S. Pat. No. 9,456,863.

With reference to FIGS. 7-9, a method of sealing and/or severing tissue with an electrosurgical forceps (e.g., electrosurgical forceps 100) is described in accordance with the present disclosure. The electrosurgical forceps 100 (FIG. 1) may be provided with the end effector 114 in an open configuration (FIG. 2A). It will be appreciated that when the end effector 114 is in the open configuration, the movable handle 122 is biased to the unactuated position by the biasing member 189 as shown in FIG. 7.

Alternatively, the electrosurgical forceps 100 (FIG. 1) may be provided with the end effector 114 in a closed configuration (FIG. 2B). To transition the end effector 114 from the closed configuration to the open configuration, the movable handle 122 is moved from the first actuated position (FIG. 8) towards the unactuated position (FIG. 7). As the movable handle 122 moves from the first actuated position, the segmented gear 212 engages the actuation gear 224 to rotate the first actuation link 220 such that the cam 238 of the second actuation link 230 moves downward and below the centerline of the outer shaft 160. Once the cam 238 is below the centerline of the outer shaft 160, the biasing member 189 urges the collar 184 distally to transition the end effector 114 to the open configuration. Additionally or alternatively, the movable handle 122 may be manually moved from the first actuated position to control the transition of the end effector 114 to the open configuration.

With the end effector 114 in the open configuration, targeted tissue (not shown) is positioned within the end effector 114. With the targeted tissue positioned within the end effector 114, the movable handle 112 is compressed towards the first actuated position. As the movable handle 122 is compressed towards the first actuated position, the actuation mechanism 200 translates the collar 184 proximally against the biasing member 189 until the end effector 114 is in the closed configuration (FIG. 2B). When the end effector 114 reaches the closed configuration, continued actuation of the movable handle 122 decouples the movable handle 122 from the actuation mechanism 200 which results in a reduction or elimination of force required to maintain the movable handle 122 in the first actuated position. In addition, the clicker tab 120a may provide audible indicia that the end effector 114 is in the closed configuration.

With the end effector 114 in the closed configuration, a clinician can release the movable handle 122 and/or relax a hand used to compress the movable handle 122. As detailed above, the actuation mechanism 200 maintains the end effector 114 in the closed configuration when the movable handle 122 is between the first and second actuated positions. With the end effector 114 maintained in the closed configuration, a clinician can verify the position of the end effector 114 (e.g., the targeted tissue is properly positioned within the end effector 114) and/or can verify the closure pressure is within a suitable range for sealing the targeted tissue.

If the position or the closure pressure is undesirable, the movable handle 122 can be moved towards the unactuated position to release the targeted tissue and the end effector 114 can be repositioned. With the end effector 114 repositioned, the movable handle 122 is compressed to the first actuated position to transition the end effector 114 to the closed configuration.

When the position of the end effector 114 and the closure pressure is confirmed by the clinician to be acceptable, the movable handle 122 is compressed to the second actuated position such that the button activation post 138 engages the depressible button 137 to activate the switch 136. When the switch 136 is activated, the end effector 114 delivers electrosurgical energy to the targeted tissue to seal the targeted tissue. With the targeted tissue sealed, the knife trigger 126 (FIG. 6) is moved to a proximal position to advance the knife blade 156 through the knife channel 158 (FIG. 2A) to sever the sealed tissue. In some embodiments, the switch 136 may be activated to deliver electrosurgical energy to the targeted tissue in such a manner to sever the sealed tissue without advancing a knife blade 156.

The movable handle 122 is then moved towards the unactuated position to transition the end effector 114 to the open configuration. As the movable handle 122 moves toward the unactuated position, the movable handle 122 may engage the knife trigger 126 to return the knife trigger 126 to the distal position. With the end effector 114 in the open configuration, the end effector 114 can be repositioned to seal and/or sever additional tissue or the electrosurgical forceps 100 can be removed from the surgical site.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A surgical device, comprising:
   a housing having a stationary handle and a movable handle pivotally supported by the housing and pivotable between an unactuated position, a first actuated position, and a second actuated position;
   an elongated shaft extending distally from the housing and defining a longitudinal axis;
   an end effector supported by a distal portion of the elongated shaft, the end effector having a pair of opposed jaw members movable between an open configuration in which the jaw members are spaced apart from one another and a closed configuration in which the jaw members are closer together; and
   an actuation mechanism configured to transition the end effector between the open configuration and the closed configuration as the movable handle is pivoted between the unactuated position and the first actuated position and to maintain the end effector in the closed configuration when the movable handle is pivoted between the first and second actuated positions, wherein the actuation mechanism includes a first actuation link, a second actuation link, and a third actuation link, the first actuation link rotatable about a first portion thereof that is secured within the housing and including a second portion of the first actuation link movable in an arc in response to rotation of the first actuation link, the second actuation link including a first portion pivotally coupled to the second portion of the first actuation link and a second portion of the second actuation link including a cam disposed within a cam slot defined in a track attached to the housing, the third actuation link including a first portion pivotally coupled to the second portion of the second actuation link and a second portion of the third actuation link coupled to a collar translatable along the longitudinal axis to transition the end effector between the open and closed configurations,
   wherein in the unactuated position of the movable handle, the cam is positioned on a first side of the longitudinal axis and in the first actuated position of the movable handle, the cam is positioned on a second side of the longitudinal axis.

2. The surgical device according to claim 1, wherein the actuation mechanism includes a segmented gear secured to the movable handle and the first actuation link rotatably disposed within the housing, the first portion of the first actuation link including an actuation gear, the segmented gear engaged with the actuation gear when the movable handle is between the unactuated position and the first actuated position and disengaged from the actuation gear when the movable handle is between the first and second actuated positions.

3. The surgical device according to claim 1, wherein the housing includes a biasing member engaged with the collar to urge the collar distally, the biasing member maintaining the cam on the second side of the longitudinal axis when the movable handle is between the first and second actuated positions.

4. The surgical device according to claim 3, wherein the biasing member is a coil spring disposed about the longitudinal axis.

5. The surgical device according to claim 3, wherein the actuation gear is disposed on the second side of the longitudinal axis.

6. The surgical device according to claim 3, wherein the cam slot has a first segment disposed on the first side of the longitudinal axis and a second segment disposed on the second side of the longitudinal axis, the second segment positioned distal of the first segment.

7. The surgical device according to claim 6, wherein the cam slot is linear.

8. The surgical device according to claim 1 wherein the collar is fixed to an outer shaft operably coupled to the end effector.

9. The surgical device according to claim 1, further comprising a knife blade and a knife trigger, the knife trigger movable when the movable handle is in the second actuated position to advance the knife blade through the end effector, the knife trigger prevented from moving when the movable handle is between the unactuated and first actuated positions.

10. A surgical device, comprising:
    a movable handle including a boss, the movable handle pivotable about the boss between an unactuated position, a first actuated position, and a second actuated position; and
    an actuation mechanism configured to translate a shaft along a longitudinal axis defined by the shaft, the actuation mechanism including:
    a segmented gear rotatably coupled to the movable handle about the boss;
    a first link having a first portion and a second portion, the first portion selectively engaged by the segmented gear and defining an opening, the second portion rotating about the opening in response to engagement between the first portion and the segmented gear;
    a second link having a first segment and a cam, the first segment rotatably coupled to the second portion of the first link;
    a track defining a cam slot that slidably receives the cam, the cam sliding within the cam slot in response to rotation of the second portion of the first link;
    a third link having a first portion rotatably coupled to the cam and a second portion; and
    a collar coupled to the second portion of the third link, the collar configured to translate the shaft in response to sliding of the cam within the cam slot, wherein the cam slot includes a first part and a second part disposed distally from the first part, the collar disposed in a first position along the longitudinal axis when the cam is in the first part of the cam slot and the collar disposed in a second position along the longitudinal axis proximal of the first position when the cam is in the second part of the cam slot, and wherein the cam is disposed on a first side of a center of the collar when positioned in the first part of the cam slot and on a second side of the center of the collar, opposite the first side, when positioned in the second part of the cam slot.

11. The surgical device according to claim 10, further comprising a biasing member engaged with the collar and configured to maintain the cam in the second part of the cam slot and to urge the cam away from the second part when the cam is positioned in the first part.

* * * * *